United States Patent [19]

Edwards et al.

[11] Patent Number: 4,780,548

[45] Date of Patent: Oct. 25, 1988

[54] PROCESS FOR THE MANUFACTURE OF MALEIC ANHYDRIDE UTILIZING CATALYSTS REACTIVATED WITH AN ESTER OF ORTHOPHOSPHORIC ACID IN THE PRESENCE OF WATER

[75] Inventors: Robert C. Edwards, Naperville; Carl A. Udovich, Joliet, both of Ill.

[73] Assignee: Amoco Corporated, Chicago, Ill.

[21] Appl. No.: 64,177

[22] Filed: Jun. 18, 1987

Related U.S. Application Data

[63] Continuation of Ser. No. 706,035, Feb. 27, 1985, abandoned, which is a continuation-in-part of Ser. No. 484,949, Apr. 14, 1983, abandoned.

[51] Int. Cl.$^4$ ............................................. C07D 307/60
[52] U.S. Cl. .................................. 549/259; 549/256; 549/257; 549/260
[58] Field of Search ................ 549/256, 257, 259, 260

[56] References Cited

U.S. PATENT DOCUMENTS 3,296,282  1/1967  Kerr ..................................... 549/259

FOREIGN PATENT DOCUMENTS 1291354  6/1969  United Kingdom .
1464198  2/1977  United Kingdom .

Primary Examiner—Mary C. Lee
Assistant Examiner—Bernard I. Dentz
Attorney, Agent, or Firm—Matthew R. Hooper; William H. Magidson; Ralph C. Medhurst

[57] ABSTRACT

A process for the reactivation of vanadium-phosphorus-oxygen catalyst with alkyl esters of phosphoric acid and water is disclosed. The catalysts are useful for the manufacture of maleic anhydride from $C_4$ hydrocarbon benzene feedstock.

10 Claims, No Drawings

PROCESS FOR THE MANUFACTURE OF MALEIC ANHYDRIDE UTILIZING CATALYSTS REACTIVATED WITH AN ESTER OF ORTHOPHOSPHORIC ACID IN THE PRESENCE OF WATER

RELATED APPLICATION

This is a continuation application of Ser. No. 706,035 filed Feb. 27, 1985, now abandoned which in turn is a continuation-in-part of Ser. No. 484,949 filed Apr. 14 1983, now abandoned.

FIELD OF THE INVENTION

The field of this invention relates to reactivation of phosphorus-vanadium catalysts, with a hydrocarbon ester of phosphoric acid, in the presence of water.

BACKGROUND

Maleic anhydride is of significant commercial interest throughout the world and is extensively used in the production of alkyd resins. It is also a versatile intermediate for chemical synthesis. Consequently, large quantities of maleic anhydride are produced each year to satisfy these needs.

In general, catalysts utilized for the oxidation of $C_4$ hydrocarbons, such as butane, butene, butadiene and benzene, to maleic anhydride are based upon vanadium and phosphorus. Various metal activators have been used to enhance the phosphorus-vanadium catalyst. The difficulty with the phosphorus-vanadium metal-promoted catalysts is that they tend to lose selectivity quite quickly. In this connection, U.S. Pat. Nos. 4,020,174; 4,094,816 and 4,089,807 teach that carbon tetrachloride can be used to reactivate the vanadium-phosphorus metal-promoted catalyst. In U.S. Pat. No. 3,296,282 and U.S. Pat. No. 3,474,041 there is described a method for the regeneration of vanadium-phosphorus oxidation catalysts used in the oxidation of olefins to make maleic anhydride. These references disclose the process of treating the catalyst with a phosphine, phosphite or phosphonate by periodically or continuously passing the phosphorus compound to the reactor, with or without interrupting the olefin feed flow. British Patent Specification No. 1,464,198 teaches regeneration of phosphorus complexes with certain phosphates. This reference does not disclose the reactivation of vanadium-phosphorus catalysts in the presence of about 1000 to about 40,000 parts per million of water in the feed gas stream as capable of being regenerated by organic phosphates and this reference does not suggest that the phosphates used in regeneration improved the color stability of the resulting maleic anhydride. Particularly, the reference does not appreciate that water in excess of 100,000 to 500,000 parts per million by weight in the feed gas stream is deleterious to the catalyst reactivation process.

We have now discovered a method for regenerating in situ vanadium-phosphorus catalyst complexes used in the vapor-phase oxidation of benzene, butane, butene or butadiene to maleic anhydride. According to our process, the vapor-phase oxidation of butane, benzene, butene or butadiene to maleic anhydride is conducted by contacting the hydrocarbon feedstock in the presence of a vanadium-phosphorus-oxygen catalyst. The catalyst is regenerated continuously or by batch method as desired during the vapor-phase oxidation of butane, benzene, butene or butadiene with an alkyl ester of orthophosphoric acid having the formula $(RO)_3P=O$, wherein R is hydrogen or a $C_1$ to $C_4$ alkyl, at least one R being a $C_1$ to $C_4$ alkyl. The preferred method is to regenerate the catalyst continuously because significantly better maleic anhydride yields are obtained.

The catalyst to be reactivated can be prepared in various ways including the one disclosed in U.S. Pat. No. 3,862,146, issued Jan. 21, 1975, having Edward M. Boghosian as its inventor. The catalyst can also be prepared according to the process disclosed in U.S. Pat. Nos. 4,418,003; 4,416,802; and 4,416,803. Alternatively, the catalyst to be reactivated can suitably be prepared from an alcohol solution which has been reacted with phosphorus pentoxide and has been saturated with an inorganic acid, such as hydrogen chloride. Other ways to prepare the catalyst are disclosed in U.S. Pat. No. 4,328,126 wherein the catalyst is made from an organic solvent system. Precipitation of the phosphorus-vanadium oxide can suitably be effected by azeotropic distillation of the organic solvent and the water of reaction and the subsequent evaporation of the organic solvent. The atomic ratio of vanadium to phosphorus can suitably be in the range of about 0.5:1 to about 1.25:1, preferably in the range of about 0.6:1 to about 1:1. The atomic ratio of phosphorus to vanadium is suitably in the range of about 2:1 to about 0.8:1, preferably about 1:1 to about 1.7:1.

The reactivation of the catalyst can also suitably be conducted by dissolving the alkyl ester of phosphoric acid in water and applying this solution in a uniform manner to the catalyst to be regenerated. This method is particularly suitable in continuous processes which utilize multi-tubular upflow reactors. In this process, the alkyl ester, in an aqueous medium comprising about 0.001 to about 90 wt. % of the alkyl ester, is sprayed as a liquid into the feed gas stream flowing to the reactor. This process has great advantages over conventional additions of regenerating agents, which entail plant shutdowns, since, in our novel process, the reactivation is conducted in situ without interrupting production or utilizing a hot oil vaporizer which tends to decompose alkyl phosphates. Our continuous process for color stabilizing maleic anhydride obtained by the vapor-phase oxidation of butane, butene, butadiene or benzene over a phosphorus-vanadium-oxygen catalyst comprises regenerating the catalyst by contacting it during the vaporphase oxidation with water and an alkyl ester of orthophosphoric acid having the formula $(RO)_3P=O$ where R is hydrogen, or a $C_1$ to $C_4$ alkyl, at least one R being a $C_1$ to $C_4$ alkyl. The continuous reactivation is applicable to phosphorus-vanadium catalysts.

This invention also comprises a process for oxidizing butane, butadiene, butene or benzene to maleic anhydride by contacting it in the presence of oxygen with the continuously reactivated catalyst in the presence of about 1000 to about 40,000 parts per million by weight of water based on the total weight of the feed gas stream, and for improving the color and color stability of maleic anhydride produced by our novel process employing continuous or batch catalyst regeneration. Generally the amount of alkyl ester added is about 0.1 to about 100,000 parts per million by weight of the reactor feed gas stream. In a preferred novel process using continuous catalyst regeneration, the amount of alkyl phosphate added is in the range of about 0.1 to about 30 parts per million by weight of the reactor feed gas stream. Higher concentrations of alkyl phosphate generally above about 30 parts per million by weight are useful in a batch catalyst regeneration process, preferably in a range of about 50 to about 100,000 parts per million by weight of reactor fed gas stream and more preferably about 1000 to about 100,000 parts per million by weight of reactor feed gas stream. The reactivation is conducted at a temperature of about 650° to about 900° F. The alkyl phosphate in a water medium comprising about 0.001 to about 90 weight percent, more preferably about 0.01 to about 50 weight percent, of the solution is contacted with the feed gas stream flowing to the reactor. If desired, the water and alkyl phosphate may be added separately to the feed gas stream instead of as a solution. Alternatively, the alkyl phosphate and water may be added directly to the butane feed prior to the mixing of the butane and air reactants. The oxidation of butane to maleic anhydride may be accomplished by contacting n-butane in low concentration in oxygen with the described catalyst. Air is entirely satisfactory as a source of oxygen, but synthetic mixtures of oxygen and diluent gases such as nitrogen may also be employed. Air enriched with oxygen may be used.

The gaseous feed stream to the oxidation reactors will normally contain air and about 0.2 to about 1.7 mole percent of n-butane, butene, butadiene or benzene. About 0.8 to about 1.5 mole percent of n-butane is satisfactory for optimum yield of maleic anhydride for the process of this invention. Although higher concentrations may be employed, explosive hazards may be encountered. Lower concentrations of butane, benzene, butadiene or butene, less than about one percent, of course, will reduce the total yield obtained at equivalent flow rates and, thus, are not normally employed for economic reasons. The flow rate of the gaseous stream through the reactor may be varied within rather wide limits, but the preferred range of operations is at the rate of about 100 to about 4000 cc of feed per cc of catalyst per hour and more preferably about 1000 to about 2400 cc of feed per cc of catalyst per hour. Lower flow rates make the butane, butene, butadiene or benzene oxidation process uneconomical. A catalyst should be effective at flow rates of about 1200 to about 2400 cc of hydrocarbon feed per cc of catalyst per hour. There are catalysts which show good promise but when subjected to the hourly space velocity designated above show very poor yields. The amount of water added is about 1000 to about 40,000 parts per million by weight of the reactor feed gas stream. The preferred amount of water added is about 5000 to about 35,000 parts per million by weight of the reactor feed gas stream. Residence times of the gas stream will normally be less than about four seconds, more preferably less than about one second, and down to a rate where less efficient operations are obtained. The flow rates and residence times are calculated at standard conditions of 760mm of mercury and at 0° C.

A variety of reactors will be found to be useful and multiple tube heat exchanger-type reactors are quite satisfactory. The tops of such reactors may vary in diameter from about one-quarter inch to about three inches, and the length may be varied from about three to about ten or more feet. The oxidation reaction is an exothermic reaction and, therefore, relatively close control of the reaction temperatures should be maintained. It is desirable to have the surface of the reactors at a relatively constant temperature and some medium is needed to conduct heat from the reactors, such as lead and the like, but it has been found that eutectic salt baths are completely satisfactory. One such salt bath is a sodium nitrate, sodium nitrite, and potassium nitrate eutectic constant temperature mixture. An additional method of temperature control is to use a metal block reactor whereby the metals surrounding the tube act as a temperature regulating body. As will be recognized by one skilled in the art, the heat exchanger medium may be kept at the proper temperature by heat exchangers and the like. The reactor or reaction tubes may be iron, stainless steel, carbon steel, nickel, glass tubes such as vycor, and the like. Both carbon steel and nickel tubes have excellent long life under the conditions of the reaction described herein. Normally, the reactors contain a preheat zone containing an inert material such as one-quarter-inch Alundum pellets, inert ceramic balls, nickel balls, or chips and the like present at about one-half to one-tenth the volume of the active catalyst present.

The temperature of reaction may be varied within some limits but, normally, the reaction should be conducted at a temperature within a rather critical range. The oxidation reaction is exothermic and once reaction is underway, the main purpose of the salt bath or other media is to conduct heat away from the walls of the reactor and control the reaction. Better operations are normally obtained when the reaction temperature employed is no greater than about 20° to about 50° F. above the salt bath temperature. The temperature of the reactor, of course, will also depend to some extent upon the size of the reactor and the hydrocarbon feedstock concentration.

The reaction may be conducted at atmospheric, superatmospheric or below atmospheric pressure. The exit pressure will be at least slightly higher than ambient pressure to ensure a positive flow from the reactor. The pressure of the inert gases must be sufficiently higher to overcome the pressure drop through the reactor.

Maleic anhydride may be recovered by a number of ways well known to those skilled in the art. For example, the recovery may be by direct condensation or by absorption in suitable media, with specific operation and purification of the maleic anhydride.

The following examples will serve to provide a fuller understanding of the invention, but it is to be understood that these examples are given for illustrative purposes only and should not be interpreted as limiting the invention in any way. In the examples, the terms "conversion", "selectivity" and "yield" are defined as follows:

$$\text{Conversion \%} = \frac{\text{Moles n-butane reacted}}{\text{Moles n-butane in feed}} \times 100$$

$$\text{Selectivity \%} = \frac{\text{Moles maleic anhydride produced}}{\text{Moles n-butane feed consumed}} \times 100$$

$$\text{Yield Wt. \%} = (\text{Conversion}) \times (\text{Selectivity}) \times 169$$

EXAMPLE 1

A used phosphorus-vanadium-oxygen catalyst gave a yield of 55 wt. % at 782° F., 2000 VHSV, and 1.5% n-butane at 115 hours on stream in a 0.62 inch internal diameter pilot reactor having a 33-inch bed. Addition of 1.6–5.0 ppm of triethylphosphate to the feed gas stream produced a maximum yield of 71 wt. % at 813° F. and the same flow conditions at 1090 hours on stream. The yield then declined to 61 wt. % at 2496 hours on stream at 818° F. with 7.4 ppm of triethylphosphate addition.

The triethylphosphate addition was then discontinued at 2497 hours. After 3048 hours, the yield was 58 wt. % at 797° F., 2000 VHSV, and 1.5% n-butane. Water was then added to the feed at a concentration of 10,000 ppm along with 1.5-13 ppm of triethylphosphate. After 4756 hours on stream, this catalyst gave a maximum yield of 73.6 wt. % at 845° F., 2000 VHSV, 1.5% n-butane, 10,000 ppm of water, and 13 ppm of triethylphosphate. In this example, the alkylphosphate ester produced a yield increase without water present. Then the treatment resulted in a yield decline. However, adding the alkylphosphate with water produced a higher maximum yield and continued treatment gave no yield decline.

As shown in this Example, the use of water with alkylphosphate esters is very important. Prolonged addition of alkylphosphate without the co-addition of water can result in a yield decline. This decline is dependent on the catalyst used. The use of water and alkylphosphate esters gives better results when compared with the use of alkylphosphates without water.

EXAMPLE 2

A 6 cc sample, 5.79 g, of spent phosphorus-vanadium-oxygen catalyst gave a 25 wt. % yield of maleic anhydride with a conversion of 91 mole% and a 17 mole% selectivity in a 0.62 inch diameter minireactor operated at 831° F. and 1200 VHSV of n-butane in synthetic air. The feed stream was passed through a water saturator to add 10,000 ppm water to the feed. At the same conditions, 0.05 cc of trimethylphosphate was injected into the feed stream for 10 seconds. After 6 days at the same conditions, the yield was 69 wt. % with a 72 mole% conversion and a 57 mole% selectivity.

EXAMPLE 3

A 6 cc sample, 5.77 g, of spent phosphorus-vanadium-oxygen catalyst gave a 44 wt. % yield of maleic anhydride with a 90 mole% conversion and a 29 mole% selectivity in a 0.62 inch diameter minireactor at 830° F. and a 1200 VHSV of 1.1% n-butane in synthetic air. The feed stream was passed through a water saturator to add 10,000 ppm water to the feed. At the same reactor conditions, 0.08 cc of triethylphosphate was injected into the feed stream for 10 seconds. After 3 days, the catalyst gave a yield of 64 wt. % with a conversion of 85 mole% and a selectivity of 44 mole% at the same reactor conditions.

EXAMPLE 4

A 6 cc sample, 6.2 g, of spent phosphorus-vanadium-oxygen catalyst gave a 38 wt. % yield of maleic anhydride with an 89 mole% conversion and a 25 mole% selectivity in a minireactor at 830° F. and 1200 VHSV of 1.1 mole % n-butane in synthetic air. The feed stream was passed through a water saturator to add 10,000 ppm water to the feed. At these same conditions, 0.16 cc of a 50/50 by volume mixture of triethylphosphate and distilled water was injected into the feed gas stream and passed over the catalyst. After 8 days at the same conditions, the yield was 72 wt. % with a conversion of 83 mole% and a selectivity of 52 mole%. More importantly, the yield after 28 days was 68 wt. % with a 79 mole% conversion and a 51 mole% selectivity. The use of water with the triethylphosphate greatly enhanced the regenerative powers of the triethylphosphate both in terms of increased yield and the maintenance of the increased yield.

EXAMPLE 5

A triethylphosphate solution in water containing 33 wt. % triethylphosphate was pumped in a closed loop through a steam heat exchanger until the pressure reached about 55 psig at a temperature of 275° F. A slip stream of this solution was then injected for 30 minutes into the feed gas stream of a maleic anhydride reactor using a spray nozzle. The use of the spray nozzle and the flash evaporation of the water produced small droplets of triethylphosphate which were easily entrained in the feed gas. Using this procedure, 0.002 g of triethylphosphate per g of catalyst was added to the reactor feed gas. The yield of maleic anhydride increased from 65 wt. % to 70 wt. % and the selectivity increased from 48 mole% to 51 mole%. A second addition of 0.002 g triethylphosphate per g of catalyst further increased the yield and selectivity to 78 wt. % and 58 mole%, respectively, at 1500 VHSV and 1.4 mole% n-butane feed.

EXAMPLE 6

Triethylphosphate was continuously added to the feed gas stream of a maleic anhydride reactor by passing a heated, pressurized inert gas stream through a heated vessel containing triethylphospate and injecting this saturated inert gas stream into the feed gas. The addition rate of the triethylphosphate was controlled by varying the temperature and/or the flow rate of the inert gas. The yield of maleic anhydride was increased from 80 wt. % to 92 wt. % and the selectivity was increased from 61 mole% to 70 mole% at 1200 VHSV and 1.4 mole% n-butane feed using this procedure to continuously apply $4 \times 10^{-3}$ g triethylphosphate per kg of catalyst per hour.

EXAMPLE 7

Triethylphosphate, 0.053 g per g of catalyst, was continuously added to the feed gas of a maleic anhydride reactor by pumping it through a steam-jacketed line and spraying it into the feed gas. Using this procedure, the yield of maleic anhydride increased from 71 wt. % to 75 wt. % after nine days at 1600 VHSV and 1.4 mole% n-butane feed.

EXAMPLE 8

Using the procedures described in Examples 5 and 6, triethylphosphate was added to a maleic anhydride catalyst. Before triethylphosphate addition, the maleic anhydride quality as measured by aged molten color averaged 65 APHA over a one-month time period ranging from 25-300 APHA. After triethylphosphate was added, the aged molten color averaged 35 APHA with a range of 20-60 APHA. Also, fractionator purges required to remove by-products and color bodies from the crude maleic anhydride decreased from 4.7% to 1.9% of the net maleic anhydride produced.

EXAMPLE 9

A phosphorus-vanadium-oxygen catalyst containing no co-metal or other promoter was prepared according to the method reported in U.S. Pat. No. 4,418,003. A 6 cc sample, 5.60 g, of this catalyst in the form of 3/16-inch by 3/16-inch cylindrical pellets was loaded into a 0.62-inch internal diameter minireactor. A 1.08 mole% n-butane in air mixture was passed through a saturator containing water and then over the catalyst at 1200 VHSV and 730-750° F. In this manner, about 10,000 ppm of water are continuously added to the reactor feed stream.

This catalyst gave a maximum maleic anhydride yield of 96 wt. % at 1200 VHSV and 731° F. after three days on stream. The yield declined to 85 wt. % at 1200 VHSV and 738° F. after 21 days on stream. At this time, the feed stream was passed through a saturator containing a 20 wt. % aqueous solution of triethylphosphate. After 33 days on stream, the yield improved to 90 wt. % at 1200 VHSV and 765° F.

The yield was maintained at 87–90 wt. % by continuously passing the feed gas stream through a 1% aqueous solution of triethylphosphate. On stream day 117, the yield was 89 wt. % at 1200 VHSV and 785° F. At this time the saturator solution was replaced with water. The yield declined to 79 wt. % at 1200 VHSV and 754° F. by stream day 152. Again, the saturator was filled with a 1% aqueous triethylphosphate solution causing the yield to improve to 90 wt. % at 1200 VHSV and 773° F. after 170 days on stream.

On day 174, the saturator solution was replaced with 100% triethylphosphate. The yield dropped to 81 wt. % at 1200 VHSV and 776° F. by day 176.

This example demonstrates that a phosphorus-vanadium-oxygen catalyst is regenerated and stabilized with triethylphosphate and water. Using only water or triethylphosphate causes the catalyst yield to decline.

EXAMPLE 10

Another 6 cc sample, 5.50 g, of the same phosphorus-vanadium-oxygen catalyst described in Example 9 was loaded into a 0.62 inch internal diameter minireactor. A 1.08 mole% n-butane in air mixture was passed through a water saturator and then over the catalyst at 1200 VHSV and 710–740° F. In this manner, about 10,000 ppm of water are continuously added to the reactor feed stream.

This catalyst sample gave a maximum maleic anhydride yield of 88 wt. % at 1200 VHSV and 720° F. after 2 days on stream. By stream day 18, the yield had declined to 79 wt % at 1200 VHSV and 730° F. At this time the water in the saturator was replaced with 100% triethylphosphate. The yield dropped to 73 wt % at 1200 VHSV and 732° F. by day 20.

As shown in Example 9, triethylphosphate and water regenerated a phosphorus-vanadium-oxygen catalyst. However, from this Example the same catalyst was not regenerated with only triethylphosphate.

We claim:

1. A continuous process for the vapor-phase oxidation of n-butane feedstock to form maleic anhydride in which n-butane is contacted in the presence of molecular oxygen or air at an hourly space velocity of about 100 to 4000 cubic centimeters of feed per cubic centimeter of catalyst per hour with a vanadium-phosphorus-oxygen catalyst wherein the catalyst is regenerated continuously or batchwise by contacting it during the vapor-phase oxidation with an alkyl ester of orthophosphoric acid having the formula $(RO)_3P=O$ where R is hydrogen or a $C_1$ to $C_4$ alkyl, at least one R being a $C_1$ to $C_4$ alkyl, wherein the amount of water added is about 1000 parts per million to about 40,000 parts per million by weight of the reactor feed gas stream and the amount of the alkyl ester added is about 0.1 parts per million to about 100,000 parts per million by weight of the reactor feed gas stream.

2. The process of claim 1 wherein the alkyl ester is triethylphosphate.

3. The process of claim 1 wherein the alkyl ester is trimethylphosphate.

4. The process of claim 1 wherein the reaction temperature is about 650° F. to about 900° F.

5. The process of claim 1 wherein a fixed-bed catalyst is used and the feedstock contains about 0.2 to about 1.7 mole percent n-butane in air and the hourly space velocity is in the range of about 1000 to about 2400 cubic centimeters of feed per cubic centimeter of catalyst per hour.

6. A continuous process for the vapor-phase oxidation of n-butane feedstock to form maleic anhydride in which n-butane is contacted in the presence of molecular oxygen or air at an hourly space velocity of about 100 to 4000 cubic centimeters of feed per cubic centimeter of catalyst per hour with a vanadium-phosphorus-oxygen catalyst wherein the catalyst is regenerated continuously or batchwise by contacting it during the vapor-phase oxidation with water and an alkyl ester of orthophosphoric acid having the formula $(RO)_3P=O$ where R is hydrogen or a $C_1$ to $C_4$ alkyl, at least one R being a $C_1$ to $C_4$ alkyl, wherein the amount of water added is about 1000 parts per million to about 40,000 parts per million by weight of the reactor feed gas stream and the amount of the alkyl ester added is about 0.1 parts per million to about 30 parts per million by weight of the total reactor feed gas stream.

7. The process of claim 6 wherein the alkyl ester is triethylphosphate.

8. The process of claim 6 wherein the alkyl ester is trimethylphosphate.

9. The process of claim 6 wherein the reaction temperature is about 650° F. to about 900° F.

10. The process of claim 6 wherein a fixed-bed catalyst is used and the feedstock contains about 0.2 to about 1.7 mole percent n-butane in air and the hourly space velocity is in the range of about 1000 to about 2400 cubic centimeters of feed per cubic centimeter of catalyst per hour.

* * * * *